United States Patent
Monck et al.

(10) Patent No.: US 6,262,106 B1
(45) Date of Patent: Jul. 17, 2001

(54) ADAMANTANECARBOXIMIDAMIDE DERIVATIVES AND THEIR USE AS NMDA ANTAGONISTS

(75) Inventors: Nathaniel Julius Thomas Monck; Roger John Gillespie; Andrew James Bird, all of Berkshire (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/600,168
(22) PCT Filed: Jan. 1, 1999
(86) PCT No.: PCT/GB99/00321
  § 371 Date: Sep. 13, 2000
  § 102(e) Date: Sep. 13, 2000
(87) PCT Pub. No.: WO99/38841
  PCT Pub. Date: Aug. 5, 1999

(30) Foreign Application Priority Data

Feb. 2, 1998 (GB) .................................................. 9802225

(51) Int. Cl.⁷ .................................................. A61K 31/38
(52) U.S. Cl. .................. 514/438; 514/631; 514/637; 564/225; 564/244; 564/247; 549/74
(58) Field of Search .................................... 564/244, 225, 564/247; 549/74; 514/438, 637, 631

(56) References Cited

U.S. PATENT DOCUMENTS 3,829,581  8/1974  Ellis ..................................... 424/327

FOREIGN PATENT DOCUMENTS 0 392 059  10/1990  (EP) .

*Primary Examiner*—Samuel Barts
(74) *Attorney, Agent, or Firm*—Foley & Lardner

(57) ABSTRACT

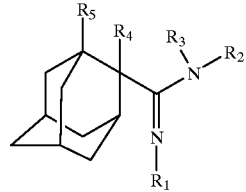

The compound of the above formula wherein R1–R5 are independently selected from hydrogen, alkyl and aryl and prodrugs thereof; and pharmaceutically acceptable salts thereof; and use of the compounds in therapy, particularly for treatment of a condition generally associated with abnormalities in glutamtergic transmission.

15 Claims, No Drawings

ADAMANTANECARBOXIMIDAMIDE DERIVATIVES AND THEIR USE AS NMDA ANTAGONISTS

This application is a 371 of PCT/GB99/00321 filed Jan. 1, 1999.

The present invention relates to compounds and compositions for use in the treatment of conditions generally associated with abnormalities in glutamatergic transmission.

The excitatory neurotransmission underlying brain function is primarily (about 80 per cent) dependent on the action of glutamate and other related neurotransmitters on specific receptors activated by the excitatory amino acids. These receptors fall into several categories, one of which is the glutamate receptor specifically sensitive to the agonist N-methyl-D-aspartate (the NMDA receptor). NMDA receptor subtypes are ubiquitously expressed in mammalian brain and have unique properties underlying their role in synaptic function and plasticity. In view of the central role of these receptors in normal central nervous system function, numerous suggestions have been made as to the utility of drugs acting at this receptor to modulate the processes underlying various disease states. The NMDA receptor has been studied with particular interest in relation to its apparent involvement in the pathophysiology of neurodegenerative diseases.

Non-competitive antagonists at this receptor should be particularly advantageous in the treatment of diseases since such compounds would have activity that should not be overcome by high levels of endogenous agonists and would act equally well independent of the endogenous agonist activating the receptor. This is important since high levels of endogenous glutamate can occur in certain pathological processes and there are a variety of different endogenous agonists that can act through a variety of specific modulatory agonist binding sites on the receptor.

A number of NMDA antagonists have been disclosed which operate by binding to the ion-channel of the NMDA receptor. The advantage of channel blockers is that they operate only on the "open" channel and therefore do not affect unactivated receptors. In addition they are effective regardless of the mechanism of receptor stimulation and their effect will not be diminished by large concentrations of endogenous agonist.

Given that the NMDA receptor plays a primary role in normal central nervous system function, it is not surprising that certain drugs acting to block or antagonise the function of this receptor affect normal function within the brain. This may be manifested as central nervous system side effects such as hallucinations, confuision, paranoia, aggression, agitation and catatonia. These side effects can be described as a psychotic state and the drugs that induce them are known as psychotomimetic NMDA antagonists. Such side effects limit the utility of these compounds in treating disease states. NMDA receptor antagonists that have efficacy in treating central nervous system disorders but without such psychotomimetic side effects would have a clear therapeutic advantage. Thus, in view of the crucial role played by the NMDA receptor in either the progression or expression of the disease pathology and process, it is an object of this invention to provide compounds for the treatment of central nervous system disorders which modulate the activity of the NMDA receptor but which are well-tolerated in the sense of having a markedly reduced propensity to induce psychotomimetic side effects.

The present invention is particularly concerned with the treatment of neurodegenerative disorders. There is a large body of evidence to suggest that either an excitotoxic or slow excitotoxic pathological over-activation of the NMDA receptor induces the death of neurons in a variety of disorders such as ischaemic stroke, other forms of hypoxic injury, haemorrhagic brain injury, traumatic brain injury, Alzheimer's disease, Parkinson's disease, Huntington's disease and other dementing diseases. There is thus clear evidence that antagonism of the NMDA receptor will reduce or prevent the neurodegeneration that underlies the disease process in these and related conditions. There is also evidence to suggest that a well-tolerated compound will allow effective symptomatic treatment of the manifestations of the disease process in these disorders as well as reducing the primary underlying neurodegeneration process. Also, it is known that disorders previously described as involving acute neurodegeneration have longer than expected elevations in glutamate release and consequently require longer than expected treatment with NMDA antagonists. There would therefore be a therapeutic advantage for new drugs which are well-tolerated and which can therefore be administered chronically.

The published literature contains references to a number of compounds and classes of compounds purported to be usefull as NMDA antagonists.

The compounds Amantadine and Memantine and related anti-viral agents have been known for many years.

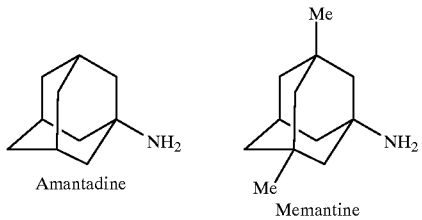

Patent applications have been filed directed to the use of Memantine in the treatment of Parkinson's Disease in the 1970s and as an NMDA antagonist in 1990 (see EP-A-0392059 and U.S. Pat No. 5061703). Furthermore, International Patent application WO94/05275 proposes the use of Amantadine and related compounds such as Memantine in the treatment and prevention of non-ischaemic, long term NMDA receptor-mediated neuronal degeneration. An increase in affinity for the NMDA receptor due to substitution of the adamantane ring of Amantadine with alkyl groups was noted and published in Kornhuber et al. (Eur. J. Pharmacol., 1991, 206, 297–300). Structure-activity relationships relating to 1-(adarnantyl)alkanamines are reported by Kroemer et al. (J. Med. Chem., 1998, 41, 393–400), by Parsons et al. (Neuropharmacology, 1995, 34, 1239–1258) and by Fytas et al. (II Farmaco, 1994, 49, 641–647).

1-(Adamantyl)amidines are disclosed as antivirals in DE-A-2306784, JP-A-7391049, DD-A-151447 and GB-1478477. 1-(Adamantyl)acetimidamide is disclosed in JP-A-120683 and GB-1478477. N-substituted-1-(adamantyl)amidines are disclosed in May et al. (Arzneim. Forsch., 1978, 28, 732–735), and the virostatic activities of the compounds reported. N-substituted-1-(adamantyl) amidines as antivirals are disclosed in Skwarski et al. (Acta. Pol. Pharm., 1988, 45, 395–399). 1- and 2-(Adamantyl) carboxamidoximes are disclosed as antivirals in U.S. Pat. No. 3,829,581.

The antiviral activities of adamantane derivatives including 1-adamantyl)carboximidamide and 1-(adamantyl) acetimidamide are reported by Inamoto et al. (J. Med. Chem., 1975, 18, 713–721), where they are compared with Amantadine.

As discussed above, psychotomimetic side-effects are observed during the use of a number of well known NMDA channel blockers and therefore it would be a considerable advantage to identify clinically well-tolerated antagonists where such side effects are minimised. Porter and Greenamyre (J. Neurochem. 1995, 64, 614–623; incorporated herein by reference) demonstrated that well-tolerated and psychotomimetic NMDA receptor channel blockers could be differentiated on the basis of their relative affinities for forebrain and cerebellar receptors irrespective of absolute affinities. Selectivity for cerebellar NMDA receptors over forebrain NMDA receptors is observed for well-tolerated compounds. The basis of this observation may be related to different populations of NMDA receptor subtypes in these brain regions.

The use of a number of known NMDA antagonists such as Dizocilpine, PCP, Cerestat and Ketamine gives rise to a number of side effects, which render these compounds unsuitable for use in treatment. In particular, administration of the compounds is associated with perceptual and cognitive disturbances of a kind that resemble naturally-occurring psychotic states.

In addition, the perceptual and cognitive side effects of the compounds become more pronounced after the onset of puberty and sexual maturation, and these compounds are therefore particularly unsuitable for the treatment of adults. This developmental change has been demonstrated empirically in both experimental animals and in man, and is paralleled in experimental animals by brain hypermetabolism.

In summary, there is a need for an NMDA antagonist which is well-tolerated and does not give rise to the side effects associated with previous clinically investigated NMDA antagonists.

A number of compounds have now been found that show affinity for the NMDA receptor and are useful in the treatment of conditions generally associated with abnormalities in glutamatergic transmission such as stroke, traumatic brain injury and neurodegenerative diseases such as Parkinson's and Alzheimer's diseases. It has also been found that the compounds have a surprisingly favourable ratio of cortical to cerebellar binding affinity which indicates that these compounds should be well-tolerated in vivo.

According to the present invention there is provided a compound of formula (1):

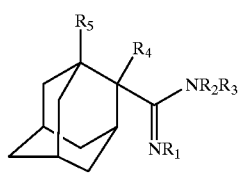

(1)

wherein $R_1$, $R_2$, $R_3$, $R_4$ and $R_5$ are independently selected from hydrogen, alkyl and aryl;
and prodrugs thereof;
and pharmaceutically acceptable salts thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl or propyl, more preferably methyl.

As used herein, the term "aryl" means an aromatic group, such as phenyl or naphthyl, or a heteroaromatic group containing one or more, preferably one, heteroatom, such as pyridyl, pyrrolyl, furanyl and thiophenyl. Preferably, the aryl group comprises phenyl.

The alkyl and aryl groups may be substituted or unsubstituted. Where substituted, there will generally be 1 to 3 substituents present, preferably I substituent. Substituents may include:

carbon containing groups such as
  alkyl,
  aryl, arylalkyl; (e.g. substituted and unsubstituted phenyl, substituted and unsubstituted benzyl);
halogen atoms and halogen containing groups such as
  haloalkyl (e.g. trifluoromethyl);
oxygen containing groups such as
  alcohols (e.g. hydroxy, hydroxyalkyl, (aryl)(hydroxy)alkyl),
  ethers (e.g. alkoxy, alkoxyalkyl, aryloxyalkyl, aryloxy),
  aldehydes (e.g. carboxaldehyde),
  ketones (e.g. alkylcarbonyl, alkylcarbonylalkyl, arylcarbonyl, arylalkylcarbonyl, arylcarbonylalkyl)
  acids (e.g. carboxy, carboxyalkyl),
  acid derivatives such as esters
    (e.g. alkoxycarbonyl, alkoxycarbonylalkyl, alkycarbonylyoxy, alkycarbonylyoxyalkyl),
  amides
    (e.g. aminocarbonyl, mono- or dialkylaminocarbonyl, aminocarbonylalkyl, mono- or dialkylaminocarbonylalkyl, arylaminocarbonyl), carbamates
    (eg. alkoxycarbonylamino, aryloxycarbonylamino, aminocarbonyloxy, mono- or dialkylaminocarbonyloxy, arylaminocarbonyloxy) and ureas
    (eg. mono- or dialkylarninocarbonylamino or arylaminocarbonylamino);
nitrogen containing groups such as
  amines (e.g. amino, mono- or dialkylamino, aminoalkyl, mono- or dialkylaminoalkyl),
  azides,
  nitriles (e.g. cyano, cyanoalkyl),
  nitro;
sulfur containing groups such as
  thiols, thioethers, sulfoxides, and sulfones
    (e.g. alkylthio, alkylsulfinyl, alkylsufonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl)
and heterocyclic groups containing one or more, preferably one, heteroatom,
  (e.g. thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, oxadiazolyl, thiadiazolyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, benzopyranyl, coumarinyl, isocoumarinyl, quinolyl, isoquinolyl, naphthridinyl, cinnolinyl, quinazolinyl, pyridopyridyl, benzoxazinyl, quinoxalinyl, chromenyl, chromanyl, isochromanyl and carbolinyl).

As used herein, the term "alkoxy" means alkyl-O- and "alkoyl" means alkyl-CO-. Alkoxy substituent groups or alkoxy-containing substituent groups may be substituted by one or more alkyl groups.

As used herein, the term "halogen" means a fluorine, chlorine, bromine or iodine radical, preferably a fluorine or chlorine radical.

As used herein the term "conditions generally associated with abnormalities in glutamatergic transmission" primarily includes ischaemic stroke, haemorrhagic stroke, subarrachnoid haemorrhage, subdural haematoma, coronary artery bypass surgery, neurosurgery, traumatic brain injury, traumatic spinal injury, Alzheimer's disease, Parkinson's disease, Huntington's disease, Pick's disease, Lewy body disease, senile dementia, spongiform encephalopathies, prion-protein induced neurotoxicity, peri-natal asphyxia, demyelinating disease, multiinfarct dementia, dementia pugilans, drug dependence, alcohol withdrawal, opiate withdrawal, motor neuron disease, multiple sclerosis, acute and chronic pain including neuropathic pain, cancer pain, trigeminal neuralgia, migraine, primary and secondary hyperalgesia, inflammatory pain, nociceptive pain, tabes dorsalis, phantom limb pain, spinal cord injury pain, central pain, post-herpetic pain, HIV pain and diabetic neuropathy. In addition, the term also includes the following conditions: epilepsy, AIDS dementia, multiple system atrophy, progressive supra-nuclear palsy, Friedrich's ataxia, autism, fragile X syndrome, tuberous sclerosis, attention deficit disorder, olivio-ponto-cerebellar atrophy, cerebral palsy, drug-induced optic neuritis, peripheral neuropathy, myelopathy, ischaemic retinopathy, glaucoma, cardiac arrest, meningitis, encephalitis, depression, bi-polar disorder, schizophrenia, psychosis, behaviour disorders, impulse control disorders, pre-eclampsia, neuroleptic malignant syndrome, chronic fatigue syndrome, anorexia nervosa, anxiety disorders, generalised anxiety disorder, panic disorder, phobias, fresh water drowning and decompression.

As used herein the term "treatment" also includes prophylactic treatment.

As used herein the term "prodrug" means any pharmaceutically acceptable prodrug of the compound of formula (1). Examples of compounds which may be useful as amidine prodrugs have been published for example by Su et al. (J. Med. Chem., 1997, 40, 4308–4318) who describe the use of N-benzyloxycarbonyl- and N-(acyloxy)methoxycarbonyl amidine derivatives, by Boykin et al. (Bioorg. Med. Chem. Lett., 1996, 6, 3017–3020) who describe the use of amidoximes and O-alkylamidoximes, and by Weller et al. (J. Med. Chem., 1996, 39, 3139–3147) who describe the use of N-alkoxycarbonylamidines as amidine prodrugs.

As used herein, the term "pharmaceutically acceptable salt" means any pharmaceutically acceptable salt of the compound of formula (1). Salts may be prepared from pharmaceutically acceptable non-toxic acids including inorganic and organic acids. Such acids include acetic, benzenesulfonic, benzoic, camphorsulfonic, citric, dichloroacetic, ethenesulfonic, fumaric, gluconic, glutamic, hippuric, hydrobrornic, hydrochloric, isethionic, lactic, maleic, malic, mandelic, methanesulfonic, mucic, nitric, pamoic, pantothenic, phosphoric, succinic, sulfuric, tartaric, oxalic, p-toluenesulfonic and the like. Particularly preferred are hydrochloric, hydrobromic, phosphoric, and sulfuric acids, and most particularly preferred is the hydrochloride salt.

The compounds of formula (1) may exist in a number of diastereomeric and/or enantiomeric forms. Reference in the present specification to "a compound of formula (1)" is a reference to all stereoisomeric forms of the compound and includes a reference to the unseparated stereoisomers in a mixture, racemic or non-racemic, and to each stereoisomer in its optically pure form.

The compounds of the present invention are active as NMDA antagonists and are well-tolerated in that side effects are minimised. Experimental data are shown in Table 1.

In the compounds of formula (1), preferably $R_1$ is hydrogen.

In the compounds of formula (1), preferably $R_2$ is hydrogen.

In the compounds of formula (1), preferably $R_3$ is hydrogen.

In a preferred embodiment of the present invention, $R_1$ is hydrogen, $R_2$ is hydrogen and $R_3$ is selected from hydrogen, alkyl and aryl.

In a further preferred embodiment of the present invention, $R_1$, $R_2$ and $R_3$ are hydrogen.

In the compounds of formula (1), preferably $R_4$ is selected from hydrogen and aryl, ore preferably from aryl, more preferably from phenyl, substituted phenyl and thiophene, and more preferably from phenyl and substituted phenyl. More preferably, $R_4$ is substituted phenyl. Where $R_4$ is substituted phenyl, $R_4$ is preferably mono- or di-substituted phenyl, preferably mono-substituted phenyl and more preferably para- or ortho-substituted phenyl. Preferably, the substituent groups are independently selected from methyl, ethyl, methoxy, chloro and fluoro.

The preferred $R_4$ groups are selected from 4-methylphenyl, 2-methylphenyl, 4-fluorophenyl, 4-chlorophenyl and 4-methoxyphenyl.

In the compounds of formula (1), preferably, $R_5$ is hydrogen.

In a preferred embodiment of the present invention, the compounds of formula (1) are selected from compounds of formula (1) where $R_1$, $R_2$, $R_3$ and $R_5$ are hydrogen; and $R_4$ is substituted phenyl.

In a further preferred embodiment of the present invention, the compounds of formula (1) are selected from 2-(4-methylphenyl)-2-adamantanecarboximidamide, 2-(2-methylphenyl)-2-adamantanecarboximidamide, 2-(4-fluorophenyl)-2-adamantanecarboximidamide, 2-(4-chlorophenyl)-2-adamantanecarboximidamide and 2-(4-methoxyphenyl)-2-adamantanecarboximidamide, and the hydrochloride salts thereof.

In an alternative embodiment of the present invention $R_4$ is selected from methyl, ethyl, cyclohexyl, benzyl and pyridyl. In a further embodiment of the present invention $R_5$ is selected from ethyl and phenyl.

The present invention also provides use of a compound of the formula (1) as defined above, and prodrugs thereof, and pharmaceutically acceptable salts thereof, in the manufacture of a medicament for use in the treatment of a condition generally associated with abnormalities in glutamatergic transmission.

The present invention further provides a method of treatment of conditions generally associated with abnormalities in glutamatergic transmission comprising administering to a patient an effective dose of a compound of formula (1) as defined above.

The present invention also provides a compound of the formula (1) as defined above, and prodrugs thereof, and pharmaceutically acceptable salts thereof for use in therapy.

According to a further aspect of the present invention there is provided a method of preparing the compounds of the present invention. Compounds of formula (1) may be prepared by conventional synthetic methods as illustrated in the Reaction Scheme.

REACTION SCHEME

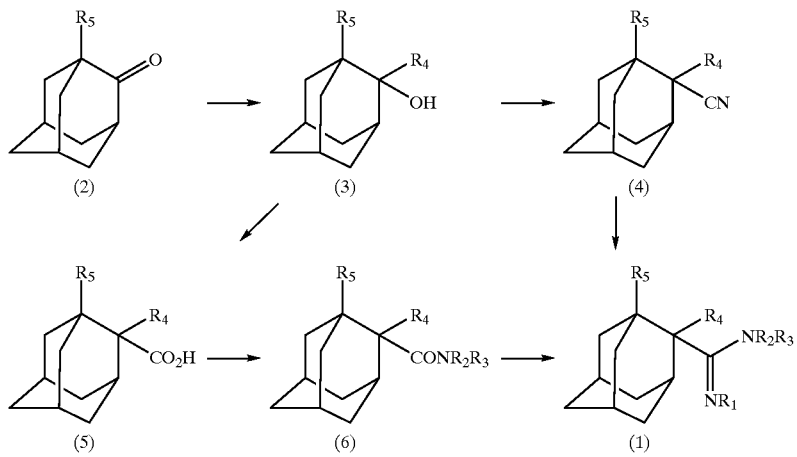

Compounds of formula (1) where $R_1$ is hydrogen may be synthesised from nitrites of formula (4) by conventional methods, for example by treatment with an amine in the presence of trimethyl aluminium in a refluxing solvent such as toluene for several days, or alternatively by treatment with HCl in dry methanol at 0° C. for several days, followed by treatment with an amine at room temperature. Nitriles of formula (4) may be synthesised from alcohols of formula (3) by conventional methods, for example by treatment with TMSCN in the presence of a Lewis Acid such as $BF_3.Et_2O$ or alternatively from carboxylic acids of formula (5) by conventional methods, for example by treatment with methanesulphonyl chloride in pyridine, followed by treatment with $NH_3$, followed by treatment with methanesulphonyl chloride in pyridine. Carboxylic acids of formula (5) may be synthesised from alcohols of formula (3) by conventional methods, for example by treatment with formic acid in the presence of concentrated sulphuric acid. Alcohols of formula (3) may be synthesised from ketones of formula (2) by conventional methods, for example by treatment with Grignard reagents. Ketones of formula (2) are commercially available or may be synthesised by conventional methods as reported, for example, by Tseng et al. (Tetrahedron, 1988, 44, 1893–1904) and by McKervey et al. (J. Chem. Soc. C, 1971, 3173–3179).

Compounds of formula (1) where $R_1$ is alkyl or aryl may be synthesised from amides of formula (6) by conventional methods, for example by treatment with thionyl chloride or trimethyloxonium tetrafluoroborate followed by an amine. Amides of formula (6) may be synthesised from carboxylic acids of formula (5) by conventional methods, for example by treatment with thionyl chloride followed by an amine.

According to a further aspect of the present invention there is provided a pharmaceutical composition comprising a compound of the present invention in combination with a pharmaceutically acceptable excipient. The compound of formula (1) may be administered in a form suitable for oral use, for example a tablet, capsule, pellet, aqueous or oily solution, suspension or emulsion; for topical use including transmucosal and transdermal use, for example a cream, ointment, gel, aqueous or oil solution or suspension, salve, patch or plaster; for nasal use, for example a snuff, nasal spray, nasal powder or nasal drops; for vaginal or rectal use, for example a pessary or suppository; for administration by inhalation, for example a finely divided powder or liquid aerosol; for sub-lingual or buccal use, for example a tablet or capsule; for occular use, for example a sterile aqueous solution or sterile ointment; or for parenteral use (including intravenous, subcutaneous, intramuscular, intravascular or infusion), for example a sterile aqueous or oil solution or suspension or emulsion, or depot injection formulation. In general the above compositions may be prepared in a conventional manner using conventional excipients, using standard techniques, including controlled release technologies, such as gelatin, lipid, gel depot, liposome and microcapsule based systems well known to those skilled in the art of pharmacy.

For oral administration, the compounds of the invention will generally be provided in the form of tablets or capsules or pellets or as an aqueous solution or suspension.

Tablets or pellets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, calcium hydrogen phosphate, cellulose derivatives and lactose, while corn starch and alginic acid are suitable disintegrating agents. Binding agents may include starch, gelatin and polyvinyl-pyrrolidone derivatives, while the lubricating agent, if present, will generally be magnesium stearate, stearic acid or talc. If desired, the tablets may be formulated or coated with a material such as glyceryl monostearate or glyceryl distearate or polymethacrylate polymers, cellulose derivatives or other pharmaceutically acceptable polymer, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Transdermal fonnulations include membrane permeation systems, multi-laminate adhesive dispersion systems and matrix dispersion systems. Transdermal delivery also includes the use of electrically aided transport, skin penetration enhancers and needle-free injection devices.

The preferred route of administration will be as an intravenous infusion, preferably over a period of up to seven days, or as an oral formulation, or as an intramuscular injection via a styrette or as a subcutaneous injection.

It will be appreciated that the dosage levels used may vary over quite a wide range depending upon the compound used, the severity of the condition exhibited by the patient and the patient's body weight. However, without commitment to a rigid definition of dosages it may be stated that a daily dosage of the active constituent (estimated as the free base) is 100 μg to 800 mg. More particularly, the preferred compounds may be administered at a preferred dose of 50–800 mg/day in single or divided doses.

The invention will now be described in detail. It will be appreciated that the invention is described by way of example only and modification of detail may be made without departing from the scope of the invention.

EXAMPLES

I. Synthetic Examples

Example 1

2-(3-Ethylphenyl)-2-adamantanecarboximidamide hydrochloride

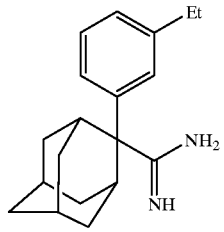

2-(3-Ethylphenyl)-2-adamantanol

A stirring mixture of magnesium turnings (0.89 g, 36.6 mmol) and iodine (catalytic) in dry THF (60 mL) was treated with 3-bromoethylbenzene (5 ML, 36.6 mmol), refluxed for 3 h, cooled to room temperature, treated with a solution of 2-adamantanone (5.0 g, 33.3 mmol) in dry THF (20 mL) and refluxed for 2 h. The mixture was cooled to room temperature, treated with 3-M HCl (20 mL), extracted with EtOAc (2×20 mL), the combined extracts were washed with water (10 mL), dried (MgSO$_4$), concentrated in vacuo and purified by chromatography [SiO$_2$; heptane-EtOAc (9:1)] to give the product (7.84 g, 92%) as a white solid: mp 63–65° C.; IR $v_{max}$ (Nujol)/cm$^{-1}$ 3442, 3281, 2921, 2855, 1604, 1451, 1101, 1043, 1009, 803 and 708; NMR $\delta_H$ (400 MHz, CDCl$_3$) 1.23 (3H, t, J 7.5 Hz), 1.61–1.70 (9H, m), 1.89 (1H, s), 2.38–2.41 (2H, m), 2.56 (2H,s), 2.65 (2H, q, J7.5 Hz), 3.46 (1H, s), 7.11 (1H, d, J7.5 Hz) and 7.24–7.36 (3H, m); Anal. Calcd for C$_{18}$H$_{24}$O: C, 84.32; H, 9.43. Found: C, 84.24; H, 9.28.

2-(3-Ethylphenyl)-2-adamantanecarbonitrile

A solution of 2-(3-ethylphenyl)-2-adamantanol (1.82 g, 7.14 mmol) in dry CHCl$_3$ (5 mL) under argon, was treated with trimethylsilyl cyanide (1.00 mL, 7.5 mmol), cooled to 0° C., treated with BF$_3$ etherate (1.10 mL, 8.57 mmol), allowed to warm to room temperature and stirred for 2 h. The mixture was treated with dilute NaHCO$_3$ (10 mL), extracted with CHCl$_3$ (2×10 mL), the combined extracts washed with water (10 mL), dried (MgSO$_4$), concentrated in vacuo and purified by chromatography [SiO$_2$; heptane-EtOAc (9:1)] to give the product (217 mg, 82%) as a colourless oil: IR $v_{max}$ (thin film)/cm$_{-1}$ 2922, 2860, 2226, 1604, 1487, 1453, 1105, 799 and 704; NMR $\delta_H$ (400 MHz, CDCl$_3$) 1.24 (3H, t, J 7.5 Hz), 1.62–1.65 (2H, m), 1.70–1.82 (5H, m), 1.98–2.04 (3H, m), 2.45 2.48 (2H, m), 2.66 (2H, q, J 7.5 Hz), 2.79 (2H, s), 7.15 (1H, d, J 7.5 Hz) and 7.25–7.34 (3H, m); Anal. Calcd for C$_{19}$H$_{23}$N: C, 85.99; H, 8.73; N, 5.28. Found: C, 85.85; H, 8.77; N, 5.23.

2-(3-ethylphenyl)-2-adamantanecarboximidamide hydrochloride

A solution of 2-(3-ethylphenyl)-2-adamantanecarbonitrile (265 mg, 1 mmol) and NH$_4$Cl (107 mg, 2 mmol) in dry toluene (5 mL) under argon was treated dropwise with 2-M trimethylaluminium in toluene (1.0 mL, 2 mmol), refluxed for 12 h, cooled to room temperature and purified directly by chromatography [SiO$_2$; EtOAc—MeOH (9:1)] to give the title compound (178 mg, 56%) as a white solid: mp >300° C.; IR $v_{max}$ (Nujol)/cm$^{-1}$ 2921, 2855, 1669, 1454, 1377, 1089, 798, 744 and 704; NMR $\delta_H$ (400 MHz, DMSO-d$_6$) 1.18 (3H, t, J 8.0 Hz), 1.55–1.69 (7H, m), 1.83 (5H, s), 2.60 (2H, q, J 8.0 Hz), 3.15 (2H, s), 7.10–7.17 (1H, m), 7.27–7.38 (3H, m) and 8.88 (4H, br s); Anal. Calcd for C$_{19}$H$_{27}$ClN$_2$.0.35 H$_2$O: C, 70.18; H, 8.59; N, 8.61. Found: C, 70.25; H, 8.41; N, 8.46.

Example 2

2-(3-Methylphenyl)-2-adamantanecarboximidamide hydrochloride

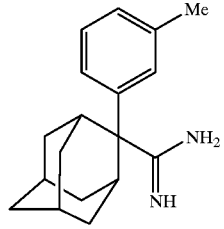

2-(3-Methylphenyl)-2-adamantanecarbonitrile

This was prepared by the method of example 1 using 2-(3-methylphenyl)-2-adamantanol in place of 2-(3-ethylphenyl)-2-adamantanol and the product (1.16 g, 66%) isolated as a white solid: mp 85–86° C.; IR $v_{max}$ (Nujol)/cm$^{-1}$ 2924, 2858, 2225, 1604, 1455, 1378, 1103, 783 and 705; NMR $\delta_H$ (400 MHz, CDCl$_3$) 1.63–1.66 (2H, m), 1.76–1.82 (5H, m), 1.99–2.05 (3H, m), 2.38 (3H, s), 2.45–2.48 (2H, m), 2.78 (2H, s), 7.10 (1H, d, J 8.0 Hz) and 7.26–7.30 (3H, m); Anal. Calcd for C$_{18}$H$_{21}$N: C, 86.01; H, 8.42; N, 5.57. Found: C, 85.82; H, 8.50; N, 5.54.

2-(3-Methylphenyl)-2-adamantanecarboximidamide hydrochloride

This was prepared by the method of example 1 using 2-(3-methylphenyl)-2-adamantanecarbonitrile in place of 2-(3-ethylphenyl)-2-adamantanecarbonitrile and the title compound (200 mg, 76%) isolated as a white solid: mp>300° C.; IR $v_{max}$ (Nujol)/cm$_{-1}$ 2923, 2855, 1667, 1455, 1376, 1240, 1092, 1043, 722 and 708; NMR $\delta_H$ (400 MHz, DMSO-d6) 1.59–1.65 (7H, m), 1.85–1.90 (5H, m), 2.31

(3H, s), 3.15 (2H, s), 7.10–7.12 (1H, m), 7.29–7.34 (3H, m), 8.79 (2H, br s) and 9.02 (2H, br s); Anal. Calcd for $C_{18}H_{25}ClN_2 \cdot 0.75\ H_2O$: C, 67.91; H, 8.39; N, 8.80. Found: C, 67.80; H, 8.31; N, 8.51.

Example 3

2-Phenyl-2-adamantanecarboximidamide hydrochloride

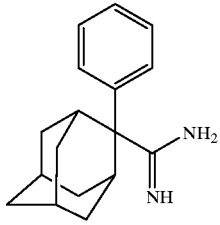

2-Phenyl-2-adamantanecarbonitrile

This was prepared by the method of example 1 using 2-phenyl-2-adamantanol in place of 2-(3-ethylphenyl)-2-adamantanol and the product (900 mg, 97%) isolated as a white solid: mp 120–122° C.; IR $v_{max}$ (Nujol)/cm$^{-1}$ 2924, 2852, 2221, 1598, 1494, 1453, 1376, 1363, 1108, 761 and 704; NMR $\delta_H$ (400 MHz, CDCl$_3$) 1.65 (2H, m), 1.73–1.83 (5H, m), 2.04 (3H, m), 2.48 (2H, m), 2.80 (2H, s), 7.32 (1H, m), 7.42 (2H, m) and 7.47 (2H, m); Anal. Calcd for $C_{17}H_{19}N$: C, 86.03; H, 8.07; N, 5.90. Found: C, 85.89; H, 8.15; N, 5.85.

2-Phenyl-2-adamantanecarboximidamide hydrochloride

This was prepared by the method of example 1 using 2-phenyl-2-adamantanecarbonitrile in place of 2-(3-ethylphenyl)-2-adamantanecarbonitrile and the title compound (148 mg, 61%) isolated as a pale yellow solid: mp>300° C.; IR $v_{max}$ (Nujol)/cm$^{-1}$ 3062, 1669, 1102, 760 and 702; NMR $\delta_H$ (400 MHz, DMSO-d$_6$) 1.6–1.7 (7H, m), 1.8–1.9 (5H, m), 3.18 (2H, s), 7.3–7.6 (5H, m), 8.78 (2H, s) and 8.85 (2H, s); Anal. Calcd for $C_{17}H_{22}N_2 \cdot 1.5\ HCl$: C, 66.07; H, 7.66; N, 9.06. Found: C, 66.28; H, 7.75; N, 8.88.

Example 4

2-(4-Methylphenyl)-2-adamantanecarboximidamide hydrochloride

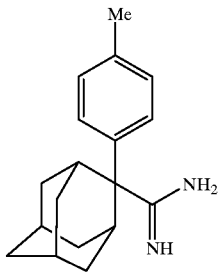

2-(4-Methylphenyl)-2-adamantanecarbonitrile

This was prepared by the method of example 1 using 2-(4-methylphenyl)-2-adamantanol in place of 2-(3-ethylphenyl)-2-adamantanol and the product (933 mg, 54%) isolated as a white crystalline solid: mp 99–100° C.; IR $v_{max}$ (Nujol)/cm$^{-1}$ 2921, 2855, 2221, 1514, 1453, 1377, 1194, 1100 and 813; NMR $\delta_H$ (400 MHz, CDCl$_3$) 1.64 (2H, d, J 13 Hz), 1.76–1.82 (5H, m), 1.99–2.05 (3H, m), 2.36 (3H, s), 2.46 (2H, d, J 13 Hz), 2.77 (2H, s), 7.23 (2H, d, J 8 Hz) and 7.36 (2H, d, J 8 Hz); Anal. Calcd for $C_{18}H_{21}N$: C, 86.01; H, 8.42; N, 5.57. Found: C, 86.11; H, 8.48; N, 5.57.

2-(4-Methylphenyl)-2-adamantanecarboximidamide hydrochloride

This was prepared by the method of example 1 using 2-(4-methylphenyl)-2-adamantanecarbonitrile in place of 2-(3-ethylphenyl)-2-adamantanecarbonitrile and the title compound (188 mg, 62%) isolated as a white solid: mp>300° C.; IR $v_{max}$ (Nujol)/cm$^{-1}$ 3278, 3112, 2929, 2855, 1670, 1455, 1377, 1022, 813 and 728; NMR $\delta_H$ (400 MHz, DMSO-d$_6$) 1.58–1.65 (7H, m), 1.84–1.90 (5H, m), 2.28 (3H, s), 3.13–3.16 (2H, m), 7.22 (2H, d, J 8.0 Hz), 7.37 (2H, d, J 8.0 Hz) and 8.85 (4H, br s); Anal. Calcd for $C_{18}H_{25}ClN_2 \cdot 0.75\ H_2O$: C, 67.91; H, 8.39; N, 8.80. Found: C, 68.09; H, 8.60; N, 8.47.

Example 5

2-(2-Methylphenyl)-2-adamantanecarboximidamide hydrochloride

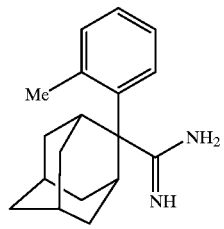

2-(2-Methylphenyl)-2-adamantanecarbonitrile

This was prepared by the method of example 1 using 2-(2-methylphenyl)-2-adamantanol in place of 2-(3-ethylphenyl)-2-adamantanol and the product (580 mg, 34%) isolated as a white solid: mp 80–81° C.; IR $v_{max}$ (Nujol)/cm$^{-1}$ 2922, 2854, 2220, 1487, 1451, 1378, 1365, 762 and 729; NMR $\delta_H$ (400 MHz, CDCl$_3$) 1.59–1.77 (6H, m), 1.97–2.03 (4H, m), 2.51–2.60 (5H, m), 2.90 (2H, br s), 7.21–7.26 (3H, m) and 7.40–7.43 (1H, m); Anal. Calcd for $C_{18}H_{21}N$: C, 86.01; H, 8.42; N, 5.57. Found: C, 85.97; H, 8.48; N, 5.56.

2-(2-Methylphenyl)-2-adamantanecarboximidamide hydrochloride

This was prepared by the method of example 1 using 2-(2-methylphenyl)-2-adamantanecarbonitrile in place of 2-(3-ethylphenyl)-2-adamantanecarbonitrile and the title compound (124 mg, 41%) isolated as a white solid: mp>300° C.; IR $v_{max}$ (Nujol)/cm$^{-1}$ 2923, 1667, 1458, 1377, 754 and 724; NMR $\delta_H$ (400 MHz, DMSO-d$_6$) 1.45–1.96 (13H, m), 2.50 (3H, s), 3.25 (1H, s), 7.12–7.28 (3H, m), 7.64 (1H, d, J 8.0 Hz) and 8.85 (4H, br s); Anal. Calcd for $C_{18}H_{24}N_2 \cdot 2.75\ HCl \cdot 0.75\ H_2O$: C, 57.95; H, 7.57; N, 7.51. Found: C, 58.05; H, 7.53; N, 7.46.

Example 6

2-(4-Fluorophenyl)-2-adamantanecarboximidamide hydrochloride

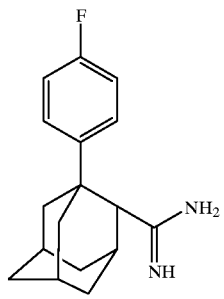

2-(4-Fluorophenyl)-2-adamantanecarbonitrile

This was prepared by the method of example 1 using 2-(4-fluorophenyl)-2-adamantanol in place of 2-(3-ethylphenyl)-2-adamantanol and the product (163 mg, 64%) isolated as a white solid: mp 81–82° C.; IR $v_{max}$ (Nujol)/cm$^{-1}$ 2924, 2861, 2223, 1601, 1510, 1502, 1467, 1454, 1242, 1166, 1104 and 835; NMR $\delta_H$ (400 MHz, CDCl$_3$) 1.62–1.65 (2H, m), 1.74 (5H, s), 1.97–2.03 (3H, m), 2.44 (2H, d, J 12.5 Hz), 2.73 (2H, s), 7.07–7.11 (2H, m) and 7.41–7.44 (2H, m); Anal. Calcd for $C_{17}H_{18}FN$: C, 79.97; H, 7.11; N, 5.48. Found: C, 80.02; H, 7.21; N, 5.47.

2-(4-Fluorophenyl)-2-adamantanecarboximidamide hydrochloride

This was prepared by the method of example 1 using 2-(4-fluorophenyl)-2-adamantanecarbonitrile in place of 2-(3-ethylphenyl)-2-adamantanecarbonitrile and the title compound (147 mg, 48%) isolated as a white solid: mp >300° C; IR $v_{max}$ (Nujol)/cm$^{-1}$ 3072, 2925, 2855, 1670, 1601, 1511, 1456, 1376, 1243, 832 and 732; NMR $\delta_H$ (400 MHz, DMSO-d$_6$) 1.62–1.66 (7H, m), 1.85 (5H, s), 3.12 (2H, s), 7.26–7.30 (2H, m), 7.51–7.55 (2H, m) and 8.90 (4H, br s); Anal. Calcd for $C_{17}H_{22}ClFN_2$.0.85 H$_2$O: C, 62.99; H, 7.37; N, 8.64. Found: C, 63.23; H, 7.11; N, 8.20.

Example 7

2-(4-Chlorophenyl)-2-adamantanecarboximidamide hydrochloride

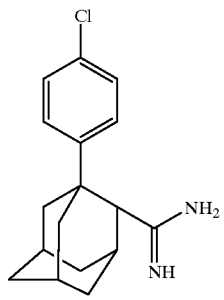

2-(4-Chlorophenyl)-2-adamantanecarbonitrile

This was prepared by the method of example 1 using 2-(4-chlorophenyl)-2-adamantanol in place of 2-(3-ethylphenyl)-2-adamantanol and the product (1.15 g, 60%) isolated as a white solid: mp 131.5–133° C.; IR $v_{max}$ (Nujol)/cm$^{-1}$ 2926, 2852, 2223, 1490, 1454, 1401, 1108, 1092, 1015 and 824; NMR $\delta_H$ (400 MHz, CDCl$_3$) 1.63–1.76 (7H, m), 1.99–2.05 (3H, m), 2.02–2.05 (2H, m), 2.74 (2H, s) and 7.38–7.42 (4H, m); Anal. Calcd for $C_{17}H_{18}ClN$: C, 75.13; H, 6.68; N, 5.15. Found: C, 74.96; H, 6.71; N, 5.13.

2-(4-Chlorophenyl)-2-adamantanecarboximidamide hydrochloride

This was prepared by the method of example 1 using 2-(4-chlorophenyl)-2-adamantanecarbonitrile in place of 2-(3-ethylphenyl)-2-adamantanecarbonitrile and the title compound (220 mg, 68%) isolated as a white solid: mp>300° C.; IR $v_{max}$ (Nujol)/cm$^{-1}$ 3065, 2924, 2855, 1669, 1495, 1376, 1095, 1012, 822 and 722; NMR $\delta_H$ (400 MHz, DMSO-d$_6$) 1.61–1.66 (7H, m), 1.85–1.98 (5H, m), 3.14 (2H, s), 7.50–7.52 (4H, m) and 8.89 (4H, br s); Anal. Calcd for $C_{17}H_{22}Cl_2N_2$.0.75 H$_2$O: C, 60.27; H, 6.99; N, 8.27. Found: C, 60.37; H, 6.88; N, 8.07.

Example 8

2-(4-Methoxyphenyl)-2-adamantanecarboximidamide hydrochloride

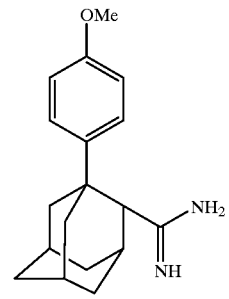

2-(4-Methoxyphenyl)-2-adamantanecarbonztrile

This was prepared by the method of example 1 using 2-(4-methoxyphenyl)-2-adamantanol in place of 2-(3-ethylphenyl)-2-adamantanol and the product (601 mg, 58%) isolated as a pale yellow solid: mp 165–166.5° C.; IR $v_{max}$ (Nujol)/cm$^{-1}$ 2918, 2855, 2220, 1609, 1512, 1458, 1377, 1298, 1260, 1183 and 1029; NMR $\delta_H$ (400 MHz, CDCl$_3$) 1.63 (2H, d, J 13.0 Hz), 1.75–1.81 (5H, m), 1.98–2.04 (3H, m), 2.45 (2H, d, J 13.0 Hz), 2.74 (2H, s), 3.82 (3H, s), 6.94 (2H, d, J 8.5 Hz) and 7.38 (2H, d, J 8.5 Hz); Anal. Calcd for $C_{18}H_{21}$,NO: C, 80.86; H, 7.92; N, 5.24. Found: C, 80.60; H, 7.94; N, 5.20.

2-(4-Methoxyphenyl)-2-adamantanecarboximidamide hydrochloride

This was prepared by the method of example 1 using 2-(4-methoxyphenyl)-2-adamantanecarbonitrile in place of 2-(3-ethylphenyl)-2-adamantanecarbonitrile and the title compound (237 mg, 74%) isolated as a white solid: mp>300° C.; IR $v_{max}$ (Nujol)/cm$^{-1}$ 3347, 3230, 3134, 2925, 2856, 1670, 1515, 1458, 1259, 1189, 1020 and 829; NMR $\delta_H$ (400 MHz, DMSO-d$_6$) 1.59–1.66 (7H, m), 1.85–1.89 (5H, m), 3.14 (2H, s), 3.76 (3H, s), 6.98 (2H, d, J 8.5 Hz), 7.41 (2H, d, J 8.5 Hz) and 8.87 (4H, br, s); Anal. Calcd for $C_{18}H_{25}ClN_2O$.1.0 H$_2$O: C, 63.80; H, 8.03; N, 8.27. Found: C, 64.08; H, 8.23; N, 7.90.

Example 9

2-(2-Thienyl)-2-adamantanecarboximidamide hydrochloride

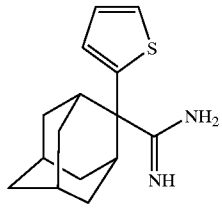

2-(2-Thieiiyl)-2-adamantanecarbonitrile

This was prepared by the method of example 1 using 2-(2-thienyl)-2-adamantanol in place of 2-(3-ethylphenyl)-2-adamantanol and the product (1.34 g, 78%) isolated as a light brown solid: mp 108–109.5° C.; IR $v_{max}$ (Nujol)/cm$^{-1}$ 2921, 2855, 2227, 1454, 1377, 1240, 1104, 820 and 728; NMR $\delta_H$ (400 MHz, CDCl$_3$) 1.70 (2H, d, J 12.5 Hz), 1.78 (3H, s), 1.97–2.05 (5H, m), 2.46 (2H, d, J 12.5 Hz), 2.64 (2H, s), 7.01–7.06 (2H, m) and 7.33 (1H, d, J 6.5 Hz); Anal. Calcd for C$_{15}$H$_{17}$NS: C, 74.03; H, 7.04; N, 5.75. Found: C, 74.19; H, 7.09; N, 5.73.

2-(2-Thienyl)-2-adamantanecarboximidamide hydrochloride

This was prepared by the method of example 1 using 2-(2-thienyl)-2-adamantanecarbonitrile in place of 2-(3-ethylphenyl)-2-adamantanecarbonitrile and the title compound (160 mg, 54%) isolated as a white solid: mp>300° C.; IR $v_{max}$ (Nujol)/cm$^{-1}$ 3073, 2922, 2854, 1670, 1455, 1377, 1246, 1100, 1084 and 698; NMR $\delta_H$ (400 MHz, DMSO-d$_6$) 1.69 (5H, s), 1.75–1.99 (7H, m), 3.16 (2H, s), 7.04–7.10 (1H, m), 7.16–7.21 (1H, m), 7.56–7.60 (1H, m) and 9.0 (4H, br s); Anal. Calcd for C$_{15}$H$_{21}$ClN$_2$S.0.25 H$_2$O: C, 59.78; H, 7.19; N, 9.30. Found: C, 59.76; H, 7.45; N, 8.71.

Example 10

2-Adamantanecarboximidamide hydrochloride

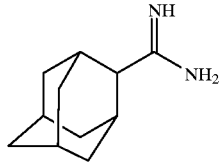

A solution of 2-adamantanecarboritrile (0.38 g, 2.37 mmol) in MeOH (15 mL) at 0° C. was saturated with HCl gas, left at 0° C. for 6 days, concentrated in vacuo, dissolved in MeOH (5 mL), saturated with ammonia gas at 0° C., left at room temperature for 3 days and concentrated in vacuo. The residue was purified by column chromatography [SiO$_2$; CH$_2$Cl$_2$-MeOH-NH$_4$OH (95:5:1)] and the resulting solid triturated with Et2O and filtered to give the title compound (65 mg, 13%) as a white crystalline solid: IR $v_{max}$ (Nujol)/cm$^{-1}$ 3072, 1678, 1651 and 692; NMR $\delta_H$ (400 MHz, DMSO-d$_6$) 1.6–1.9 (12H, m), 2.38 (2H, s), 2.85 (1H, s), 8.56 (2H, br s) and 9.00 (2H, br s).

Example 11

N-(2-Dimethylaminoethyl)-2-adamantanecarboximidamide hydrochloride

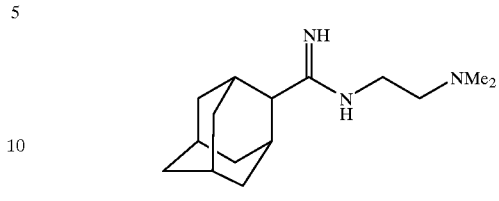

This was prepared from 2-adamantanecarbonitrile by the method of example 10 using N,N-dimethylethylenediamine (1 eq) in place of ammonia and the title compound isolated (15%) as a white crystalline solid: IR $v_{max}$ (Nujol)/cm$^{-1}$ 3219, 3076, 2779, 2695, 1688, 1608, 1126, 1037 and 799; NMR $\delta_H$ (400 MHz, DMSO-d$_6$) 1.5–1.7 (6H, m), 1.7–1.9 (6H, m), 2.2–2.3 (6H, m), 2.41 (2H, s), 2.5–2.6 (2H, m), 2.85 (2H, s), 3.4–3.5 (2H, m), 8.66 (2H, br s) and 9.17 (1H, br s).

II. NMDA Receptor Binding

The NMDA receptor contains several distinct binding domains that can regulate opening of the cationic channel. The phencyclidine (PCP) site of the NMDA receptor can be radiolabelled with [$^3$H]-(+)-5-methyl-10,11-dihydro-5H-dibenzo[a,d]cyclohepten-5,10-imine hydrogen maleate, [$^3$H-MK-801]. The following describes the procedure for determining the affinity of compounds for the PCP site in rat cortical or cerebellar membranes.

Frozen rat cortex or cerebellum, homogenized in 10 volumes of ice-cold 0.32-M. sucrose is centrifuged at 1,000 g for 12 min and the supernatant stored on ice whilst the pellet is resuspended, rehomogenized and recentrifuged twice more. The three final supernatants are pooled and centrifuged at 30,000 g for 40 min at 4° C. to yield P$_2$ pellets. These are resuspended in ice-cold distilled water, and centrifuged at 30,000 g for 50 min at 4° C. Following three further washes in distilled water, the P$_2$ pellets are stored at –20° C. for at least 18 h. On the day of the assay, membrane pellets are thawed at room temperature, resuspended in ice-cold distilled water and centrifuged at 30,000 g for 20 min. The pellets are resuspended in 50-mM tris-HCl (pH:7.4) and recentrifuged twice more before being resuspended in tris-HCl for immediate use in the assay. Binding assays are performed at equilibrium in a total volume of 200 $\mu$L, containing [$^3$H]-MK-801 (5-nM final conc.), 10-$\mu$M glutamate, 10-$\mu$M glycine, 160 $\mu$L of membrane preparation and additional drugs where appropriate. Non-specific binding is determined using MK-801 (10-$\mu$M). The assay is incubated for 120 min at room temperature. The incubation is terminated by rapid filtration through Whatman GF/B filters (pre-soaked in 0.1% PEI solution). The assay tubes and filters are washed five times with 1 mL of ice-cold assay buffer. The filters are placed in poly-Q mini vials with approximately 5 mL of scintillation fluid. The vials are then shaken and left for at least 8 h before being counted on a liquid scintillation counter. To determine the free ligand concentration 3 aliquots (20 $\mu$L) of the [$^3$H]-MK-801 working solution are also counted. Concentration response data for drugs is analysed using a 4 parameter equation fitted by non-linear regression. This yields the half maximally effective drug concentration (IC$_{50}$) and Hill coefficient.

The data obtained from these assays are presented in Table 1. The data clearly demonstrate that the compounds of the invention are active as NMDA antagonists and have favourable ratios of cortical to cerebellar binding affinity indicating that the compounds should be well-tolerated in vivo.

TABLE 1

Binding Affinities at Cortical and Cerebellar NMDA Receptors

| Compound | $IC_{50}$ Cortex ($\mu$M) | $IC_{50}$ Cerebellum ($\mu$M) | Ratio |
| --- | --- | --- | --- |
| Example 4 | 105 | 56 | 1.9 |
| Example 5 | 53 | 31 | 1.7 |
| Example 6 | 44 | 25 | 1.8 |
| Example 7 | 59 | 34 | 1.7 |
| Example 8 | 45 | 22 | 2.0 |

What is claimed is:

1. A compound of the formula (1):

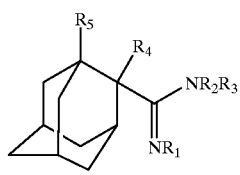

(1)

wherein:

$R_1$, $R_2$, $R_3$, R4, and $R_5$ are independently selected from hydrogen, alkyl and aryl;

and pharmaceutically acceptable salts thereof.

2. A compound according to claim 1 wherein one or both of $R_1$ and $R_2$ are hydrogen.

3. A compound according to claim 1 wherein $R_3$ is selected from hydrogen, alkyl and aryl.

4. A compound according to claim 1 wherein $R_3$ is hydrogen.

5. A compound according to claim 1 wherein $R_4$ is hydrogen or aryl.

6. A compound according to claim 1 wherein $R_4$ is substituted phenyl.

7. A compound according to claim 6 wherein said phenyl group is substituted by one or more substituent groups selected from the group consisting of methyl, ethyl, methoxy, chloro and fluoro.

8. A compound according to claim 6 wherein $R_4$ is a mono-substituted phenyl and is a para- or ortho-substituted phenyl.

9. A compound according to claim 1 wherein $R_4$ is selected from the group consisting of 4-methyiphenyl, 2-methyiphenyl, 4-fluorophenyl, 4-chlorophenyl and 4-methoxyphenyl.

10. A compound according to claim 1 wherein $R_4$ is phenyl or thiophene.

11. A compound according to claim 1 wherein $R_5$ is hydrogen.

12. A compound according to claim 1 wherein $R_1$, $R_2$, $R_3$ and $R_5$ are hydrogen; and $R_4$ is substituted phenyl.

13. A compound according to a claim 1 selected from the group consisting of:

2-(4-methylphenyl)-2-adamantanecarboximidamide;

2-(2-methylphenyl)-2-adamantanecarboximidamide;

2-(4-fluorophenyl)-2-adamantanecarboximidamide;

2-(4-chlorophenyl)-2-adamantanecarboximidamide; and 2-(4-methoxyphenyl)-2-adamantanecarboximidamide.

14. A pharmaceutical composition comprising a compound according to claim 1 in combination with a pharmaceutically acceptable excipient.

15. A method of treatment of a condition generally associated with abnormalities in glutamatergic transmission by adminstrating to a patient in need of such treatment of a pharmaceutically effective dose of a compound of formula (1) as defined in claim 1.

* * * * *